United States Patent
Osorio et al.

(10) Patent No.: US 10,803,979 B2
(45) Date of Patent: Oct. 13, 2020

(54) METHODS AND SYSTEMS FOR SECURE ACQUISITION AND TRANSMISSION OF AN IMAGE

(71) Applicant: MD Cloud Practice Solutions, L.L.C., Dallas, TX (US)

(72) Inventors: Federico Osorio, Dallas, TX (US); Andres Gutierrez Ovalles, Dallas, TX (US)

(73) Assignee: MD Cloud Practice Solutions, L.L.C., Dallas, TX (US)

( * ) Notice: Subject to any disclaimer, the term of this patent is extended or adjusted under 35 U.S.C. 154(b) by 0 days.

(21) Appl. No.: 16/505,320

(22) Filed: Jul. 8, 2019

(65) Prior Publication Data
US 2019/0333615 A1 Oct. 31, 2019

Related U.S. Application Data

(63) Continuation of application No. 14/879,248, filed on Oct. 9, 2015, now Pat. No. 10,388,408.
(Continued)

(51) Int. Cl.
| | |
|---|---|
| G06F 13/00 | (2006.01) |
| G16H 10/60 | (2018.01) |
| H04L 29/08 | (2006.01) |
| H04W 12/06 | (2009.01) |
| G16H 40/20 | (2018.01) |
| G06F 21/62 | (2013.01) |
| G06F 19/00 | (2018.01) |
| G06F 21/60 | (2013.01) |

(Continued)

(52) U.S. Cl.
CPC ........... *G16H 10/60* (2018.01); *G06F 19/328* (2013.01); *G06F 21/606* (2013.01); *G06F 21/6245* (2013.01); *G16H 40/20* (2018.01); *H04L 67/143* (2013.01); *H04W 12/02* (2013.01); *H04W 12/06* (2013.01); *H04L 63/0428* (2013.01)

(58) Field of Classification Search
CPC .... G06F 19/322; G06F 19/328; G06F 21/606; G06F 21/6245; H04W 12/02; H04W 12/06; G16H 10/60; G16H 40/20; H04L 67/143; H04L 63/0428; H04L 63/08; H04L 9/0894; H04L 2209/80; H04L 2209/88
USPC .................. 709/227, 228, 220–222; 726/26; 713/165, 193
See application file for complete search history.

(56) References Cited

U.S. PATENT DOCUMENTS

| | | |
|---|---|---|
| 3,916,095 A | 10/1975 | Weber et al. |
| 5,671,246 A | 9/1997 | McIntyre |

(Continued)

*Primary Examiner* — Kenneth R Coulter

(57) ABSTRACT

Methods and systems allow secure acquisition and transmission of images by a mobile communication device. The method includes acquiring an image by the mobile device and allocating volatile memory space in the mobile device for a defined session. The image may be acquired by a digital camera built in the mobile device. The method includes digitally storing the acquired image in the allocated volatile memory space. The method includes encrypting and transmitting the stored image using a secure transmission protocol during the session. The method includes de-allocating the volatile memory space at the termination of the session. The de-allocation of the volatile memory space may cause the digitally stored image to be erased from the volatile memory space. Thus, the stored image is not persistently retained by the mobile device.

15 Claims, 2 Drawing Sheets

Related U.S. Application Data

(60) Provisional application No. 62/062,601, filed on Oct. 10, 2014.

(51) Int. Cl.
  *H04W 12/02* (2009.01)
  *H04L 29/06* (2006.01)

(56) References Cited

U.S. PATENT DOCUMENTS

| | | |
|---|---|---|
| 6,128,621 A | 10/2000 | Weisz |
| 6,237,079 B1 | 5/2001 | Stoney |
| 7,430,671 B2 | 9/2008 | Graves et al. |
| 8,166,210 B2 | 4/2012 | Aoyama |
| 8,316,460 B1 | 11/2012 | Wang et al. |
| 10,388,408 B2 * | 8/2019 | Osorio .................. G16H 10/60 |
| 2003/0100373 A1 | 5/2003 | Fujimoto et al. |
| 2003/0154398 A1 | 8/2003 | Eaton et al. |
| 2003/0226006 A1 | 12/2003 | Ballard |
| 2004/0221788 A1 | 2/2004 | Shizukuishi |
| 2004/0162831 A1 | 8/2004 | Patterson |
| 2005/0223222 A1 | 10/2005 | Graves et al. |
| 2009/0230179 A1 | 9/2009 | Livolsi et al. |
| 2011/0223970 A1 | 9/2011 | Mori et al. |
| 2013/0096938 A1 * | 4/2013 | Stueckemann .......... G06F 19/34 705/2 |
| 2014/0180705 A1 * | 6/2014 | Stueckemann .......... G06F 19/34 705/2 |
| 2015/0015911 A1 | 1/2015 | Shimizu |
| 2015/0028578 A1 | 1/2015 | Pawlik et al. |
| 2015/0154418 A1 * | 6/2015 | Redberg ................ G06F 21/602 713/165 |
| 2015/0278474 A1 * | 10/2015 | Stueckemann ..... G06F 19/3456 705/2 |
| 2015/0363611 A1 * | 12/2015 | Redberg ................ G06F 21/602 713/165 |
| 2016/0037057 A1 | 2/2016 | Westin et al. |
| 2016/0103782 A1 | 4/2016 | Osorio et al. |
| 2016/0103964 A1 | 4/2016 | Osorio et al. |
| 2016/0104000 A1 | 4/2016 | Osori et al. |

* cited by examiner

METHODS AND SYSTEMS FOR SECURE ACQUISITION AND TRANSMISSION OF AN IMAGE

CROSS-REFERENCE TO RELATED APPLICATIONS

This application is a continuation of U.S. patent application Ser. No. 14/879,248 filed by Osorio, et al., on Oct. 9, 2015, entitled "METHODS AND SYSTEMS FOR SECURE TRANSMISSION AND RECEPTION OF DATA BETWEEN A MOBILE DEVICE AND A CENTRAL COMPUTER SYSTEM," which issued as U.S. Pat. No. 10,388,408, and claims the benefit of U.S. Provisional Application Ser. No. 62/062,601, filed by Osorio, et al., on Oct. 10, 2014, entitled "Multi-feature Mobile Software Application that Generate [sic.] a Secure Environment to Capture Data under a HIPAA/Hitech Complaint [sic.] Protocol," with each of the above applications being commonly assigned with this application and incorporated herein by reference in their entirety.

TECHNICAL FIELD

The disclosure relates to methods and systems for secure acquisition and transmission of image.

BACKGROUND

The Health Insurance Portability and Accountability Act (HIPAA) requires healthcare providers (e.g., physicians), hospitals, health insurance companies and other businesses associated with the healthcare industry that receive protected health information (PHI) to implement control of access to computer systems and networks that store PHI. HIPAA requires that computer systems that store PHI are protected from intrusion. Also, HIPAA requires any communication containing PHI transmitted electronically over open networks is encrypted to prevent unauthorized interception.

Since healthcare providers and other businesses associated with the healthcare industry typically maintain computer systems to store PHI, they must ensure that PHI is protected from intrusions. Also, healthcare providers and health insurance companies must ensure that any electronically transmitted PHI is protected from unauthorized interception. If PHI is stolen by intrusion of computer systems or if PHI is intercepted during transmission, businesses may face legal and financial liabilities. Existing systems and methods generally do not allow secure acquisition and transmission of images which may contain PHI.

SUMMARY

In one aspect, the disclosure provides a method for secure acquisition and transmission of an image by a mobile communication device. In one example, the method includes: (1) acquiring an image by the mobile device, (2) allocating volatile memory space in the mobile device for a session, (3) digitally storing the acquired image in the allocated volatile memory space, (4) transmitting the digitally stored image in the mobile device using a secure transmission protocol during the session, and (5) de-allocating the volatile memory space at the termination of the session.

In another aspect, the disclosure provides a system for secure acquisition and transmission of an image. In one example, the system includes: (1) a mobile communication device configured to communicate over a communication network, wherein the mobile communication device has (1A) at least one processor, (1B) a volatile memory space allocated by the processor for a defined session and de-allocated at the termination of the session, and (1C) a digital camera configured to acquire an image and to store the acquired image in the allocated volatile memory space, wherein the mobile communication device transmits the stored image using a secure transmission protocol during the session.

In yet another embodiment, the disclosure provides another A system for secure acquisition and transmission of an image. In one example, this system includes: (1) a mobile communication device configured to communicate over a communication network, wherein the mobile communication device includes (1A) at least one processor, (1B) a volatile memory space allocated by the processor for a defined session and de-allocated at the termination of the session, and (1C) a digital camera configured to acquire an image and to store the acquired image in the allocated volatile memory space. The system also includes: (2) a server, wherein the mobile communication device transmits, during the session, the stored image to the server over the communication network using a secure transmission protocol, and wherein the de-allocation of the volatile memory space causes the stored image to be erased from the volatile memory space.

The foregoing has outlined rather broadly the features and technical advantages of the present disclosure so that those skilled in the art may better understand the detailed description that follows. Additional features and advantages of the disclosure will be described hereinafter that form the subject of the claims. Those skilled in the art will appreciate that they may readily use the conception and the specific embodiment disclosed as a basis for modifying or designing other structures for carrying out the same purposes of the present disclosure. Those skilled in the art will also realize that such equivalent constructions do not depart from the spirit and scope of the disclosure in its broadest form.

BRIEF DESCRIPTION

Reference is now made to the following descriptions taken in conjunction with the accompanying drawings, in which.

DETAILED DESCRIPTION

Figure 1:
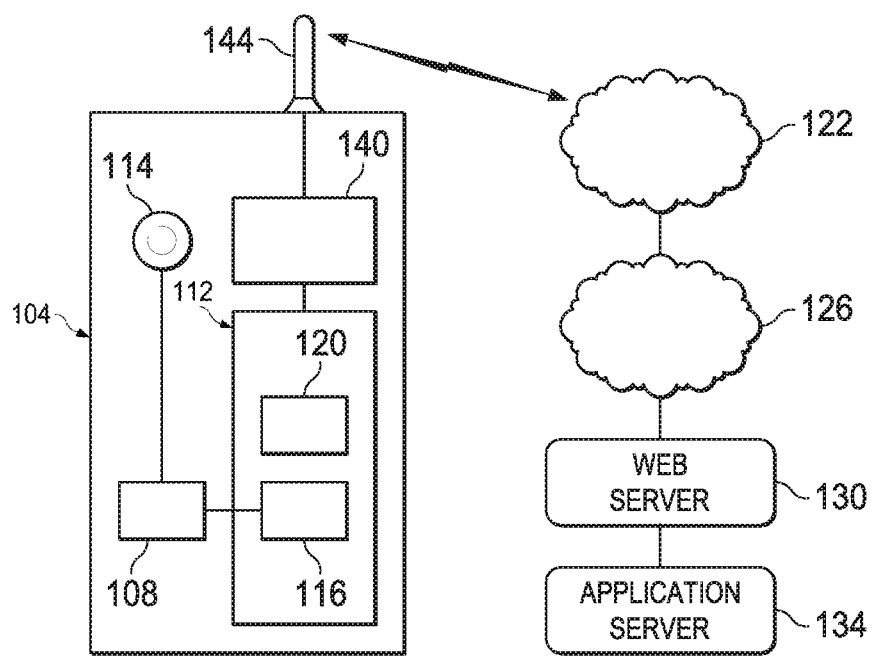
FIG. 1 is a schematic block diagram of a communication system in which embodiments of the disclosure can be implemented.

Before undertaking the DETAILED DESCRIPTION, it may be advantageous to set forth definitions of certain words or phrases used throughout this patent document: the terms "include" and "comprise," as well as derivatives thereof, mean inclusion without limitation; the term "or" is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, whether such a device is implemented in hardware, firmware, software or some combination of at least two of the same. It should be noted that the functionality associated with any particular controller may be centralized or distributed, whether locally or remotely. Definitions for certain words and phrases are provided throughout this patent document, and those of ordinary skill in the art will understand that such definitions apply in many, if not most, instances to prior as well as future uses of such defined words and phrases. While some terms may include a wide variety of embodiments, the appended claims may expressly limit these terms to specific embodiments.

FIGS. 1-5, discussed below, and the various embodiments used to describe the principles of the present disclosure are by way of illustration only and should not be construed in any way to limit the scope of the disclosure. Those skilled in the art will recognize that the principles of the disclosure may be implemented in any suitably arranged device or a system. The numerous innovative teachings of the present disclosure will be described with reference to non-limiting embodiments.

Various disclosed embodiments provide methods and systems for secure acquisition and transmission of images. The acquisition and transmission of images can be between a mobile device and a central computer system. The mobile device is configured to transmit the images securely over a communication network which may, for example, include a wireless network, a wired network, and/or a wide area network (e.g., Internet). The central computer system may be a server (e.g., application server, database server) a desktop computer, a central processor or any other type of data processing system. The mobile device and the central computer system may communicate using a secure transmission protocol (STP).

According to disclosed embodiments, an application executable on a mobile communication device allows secure acquisition and transmission of images in compliance with Health Insurance Portability and Accountability Act (HIPAA). Healthcare providers may implement the disclosed embodiments to securely acquire and transmit images containing protected health information (PHI). For example, healthcare providers may implement the disclosed embodiments to transmit images to health insurance companies in order to receive reimbursement for services provided or to receive pre-approval for services. Medical laboratories may implement the disclosed embodiments to transmit images containing laboratory reports to patients or other healthcare providers. For example, disclosed embodiments can comply with the Health Information Technology for Economic and Clinical Health (HITECH) Act.

FIG. 1 is a schematic block diagram of a communication system 100 in which embodiments of the disclosure can be implemented. The system 100 includes a mobile communication device 104 which may take the form of a mobile phone, a laptop computer, a tablet computer or the like. The mobile device 104 is configured to wirelessly communicate with other communication devices via a communication network 122. The network 122 may be a mobile cellular network such as a 3GPP network or other CDMA/GSM network. The network 122 may be linked to another network 126 such as the Internet 126.

The system 100 includes a web server 130 and an application server 134 connected to the Internet 126. The mobile device 104 may communicate with the web server 130 and the application server 134 over the networks 122 and 126. For example, the mobile device 104 may retrieve one or more web pages from the web server 130 and may access one or more applications from the application server 134.

The mobile device 104 includes a processor 108 connected to a memory 112. The processor 108 may be of the type generally used in mobile devices such as those manufactured by Intel Corporation or ARM Holdings.

According to disclosed embodiments, the memory 112 comprises a non-volatile memory 116 and a volatile memory 120. In the non-volatile memory 116, any data stored is persistently retained even after electrical power is removed from the non-volatile memory 116. Thus, any data stored in the non-volatile memory 116 is not erased following removal of electrical power. In contrast, any data stored in the volatile memory 120 is erased, and thus lost, after electrical power is removed from the volatile memory 120. Thus, any data stored in the volatile memory 120 is not persistently retained after removal of electrical power.

The mobile device 104 also includes a digital camera 114 configured to acquire images. The acquired images are stored in the memory 112. The mobile device 104 also includes a transceiver 140 coupled to an antenna 144. The transceiver 140 and the antenna 144 allow the mobile device 104 to wirelessly transmit and receive data over a wireless network such as the network 122. The mobile device 104 can include additional components, such as a keypad or an optical scanner. In some applications the digital camera 114 can function as a scanner.

Figure 2:
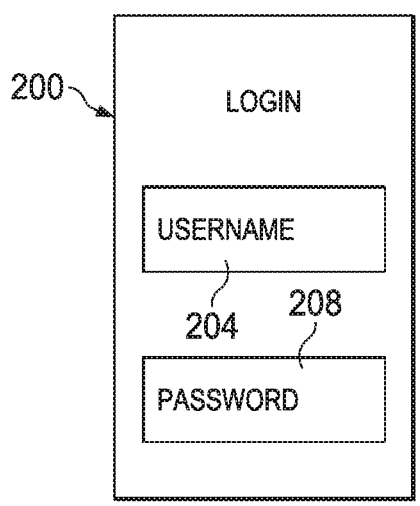
FIG. 2 illustrates an application executable on the mobile device according to disclosed embodiments.

According to disclosed embodiments, an application executable on a mobile communication device allows secure acquisition and transmission of images in compliance with HIPAA. FIG. 2 illustrates an application 200 executable on the mobile device 104. The application 200 may reside in the mobile device 104 or may reside remotely such as, for example, in the application server 134. When the application 200 resides in the application server 134, the mobile device 104 may access the application over the networks 122 and 126.

Figure 3:
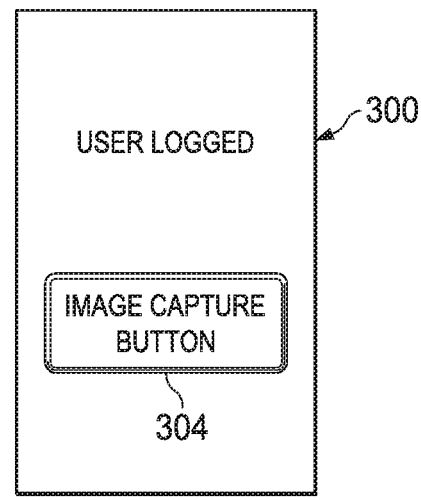
FIG. 3 illustrates the application with an image capture button.
Figure 4:
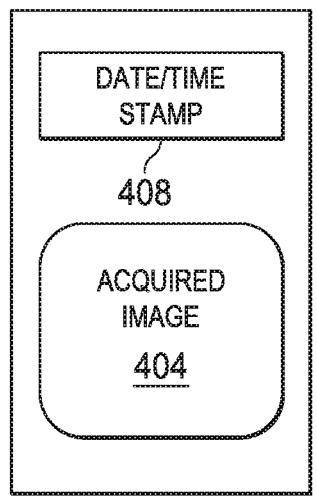
FIG. 4 shows an acquired image displayed on a mobile device.

The application 200 provides a username 204 field and a password 208 field displayed on the mobile device 104. A user can login by entering a username and a password. Upon successful login a connection is established with a secure server such as the server 130 and the server 134 over the networks 122 and 126. Once the user is logged on, a web page 300 is displayed which has an image capture button 304 as shown in FIG. 3. The user can press the image capture button 304 to activate the digital camera 114 of the mobile device 104 to acquire an image. FIG. 4 shows an acquired image 404 including a date and time stamp 408 which are displayed on the mobile device 104.

According to disclosed embodiments, a volatile memory space in the volatile memory 120 is allocated by the processor 108 for a defined session and de-allocated at the termination of the session. The session is defined for a predetermined time period. According to disclosed embodiments, the volatile memory space may be allocated by marking portions of it as being allocated to the application 200 in a memory allocation table and de-allocated by marking those portions as unallocated at the termination of the session and perhaps also overwriting it. Alternatively, the volatile memory space may be allocated by applying electrical power to the volatile memory 120 and de-allocated by removing electrical power at the termination of the session.

Volatile memory space that is temporarily allocated to an application is sometimes called "scratchpad" memory. In the context of certain mobile device operating systems commercially available from Apple Incorporated of Cupertino, Calif. (e.g., OS X®), such temporarily allocated volatile memory is called a "sandbox" and is designed to prevent applications from interfering with one another or the operating system, except as the operating system permits.

According to disclosed embodiments, the acquired image is stored in the allocated volatile memory space. The volatile memory space may be a random access memory (RAM). In some examples, access to the acquired image can be restricted or otherwise limited to the application 200 only, wherein all other applications in the mobile device 104 are prevented from accessing or using the data.

The stored image is then encrypted and transmitted to a remote server using a secure transmission protocol. For example the image may be encrypted and transmitted to the application server 134 over the networks 122 and 126. In accordance with the secure transmission protocol, at the remote server the encrypted image is authenticated upon reception.

According to disclosed embodiments, after the termination of the session, the volatile memory space is de-allocated which causes the stored image to be erased from the volatile memory space. The volatile memory space is de-allocated by marking the volatile memory space as unallocated at the termination of the session and perhaps overwriting it. Consequently, the acquired image is not persistently retained in the mobile device 104 after the termination of the session.

Thus, it will be appreciated that the disclosed embodiments provide secure acquisition and transmission of images in compliance with HIPAA. Since the acquired images are erased from the volatile memory after the defined session, and thus not persistently retained by the mobile device 104, the data is protected from intrusion and misappropriation. Also, because the transmitted images are encrypted, they are prevented from unauthorized interception.

Figure 5:
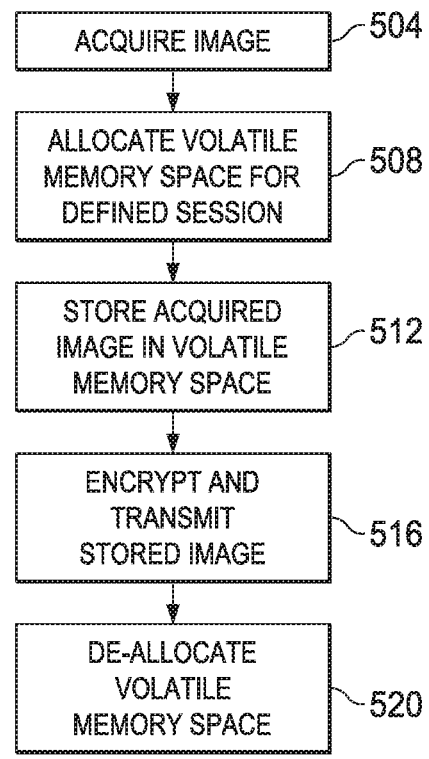
FIG. 5 is a flow diagram of the method according to disclosed embodiments.

FIG. 5 is a flow diagram of the method according to disclosed embodiments. In block 504, an image is acquired by a mobile device. The image may, for example, be the image of a document containing protected healthcare information of a patient.

In block 508, a volatile memory space is allocated in the mobile device for a defined session. As discussed before, the volatile memory space may be a random access memory allocated for a predetermined time period by marking it as allocated or applying electrical power to it.

In block 512, the acquired image is digitally stored in the allocated volatile memory space. Access to the allocated volatile memory space during the defined session can be restricted or limited to a single computer program. All other computer programs in the mobile device can be prevented from accessing the allocated volatile memory space during the defined session.

In block 516, the stored image is encrypted, and the encrypted image is transmitted using a secure transmission protocol. The image can be transmitted over a communication network, such as a network that includes a wireless network, a wired network, and/or the Internet.

In block 520, the volatile memory space is de-allocated at the termination of the session. The de-allocation of the volatile memory space causes the digitally stored image to be erased from the volatile memory space. Thus, the digitally stored image is not persistently retained by the mobile device. As discussed before, the volatile memory space may be de-allocated by marking it as de-allocated or removing electrical power from the volatile memory space. In one example, the memory space is a random access memory (RAM).

Various disclosed embodiments are directed to methods and systems for secure acquisition and transmission of images by a mobile communication device. The method includes acquiring an image by the mobile device and allocating volatile memory space in the mobile device for a defined session. The image may be acquired by a digital camera built in the mobile device. The method includes digitally storing the acquired image in the allocated volatile memory space.

The method includes encrypting and transmitting the stored image using a secure transmission protocol during the session. The method includes de-allocating the volatile memory space at the termination of the session. The de-allocation of the volatile memory space causes the digitally stored image to be erased from the volatile memory space. Thus, the stored image is not persistently retained in the mobile device, including any persistent memory space that may have been set aside for the storage of images.

According to disclosed embodiments, the volatile memory space is allocated by applying electrical power to the volatile memory and de-allocated by removing electrical power. The volatile memory space may be a random access memory (RAM).

According to disclosed embodiments, the encrypted image is transmitted to a remote server. Upon reception of the image by the remote server, the image is authenticated according to the secure transmission protocol.

According to disclosed embodiments, a system for secure acquisition and transmission of an image includes a mobile communication device configured to communicate over a communication network. The mobile communication device includes at least one processor. The mobile device includes a volatile memory space allocated for a defined session and de-allocated at the termination of the session. The mobile device includes a digital camera configured to acquire an image and to store the acquired image in the allocated volatile memory space.

According to disclosed embodiments, the stored image is encrypted and transmitted using a secure transmission protocol during the session. At the termination of the session, the volatile memory space is de-allocated, and wherein the de-allocation of the volatile memory space causes the stored image to be erased from the volatile memory space. Thus, the de-allocation of the volatile memory space causes the stored image to not be persistently retained in the mobile device, i.e., non-persistent retention.

Those skilled in the art will recognize that, for simplicity and clarity, the full structure and operation of all systems suitable for use with the present disclosure is not being depicted or described herein. Instead, only so much of a system as is unique to the present disclosure or necessary for an understanding of the present disclosure is depicted and described. The remainder of the construction and operation of the disclosed systems may conform to any of the various current implementations and practices known in the art.

Of course, those of skill in the art will recognize that, unless specifically indicated or required by the sequence of operations, certain steps in the processes described above may be omitted, performed concurrently or sequentially, or performed in a different order. Further, no component, element, or process should be considered essential to any specific claimed embodiment, and each of the components, elements, or processes can be combined in still other embodiments.

It is important to note that while the disclosure includes a description in the context of a fully functional system, those skilled in the art will appreciate that at least portions of the mechanism of the present disclosure are capable of being distributed in the form of instructions contained within a machine-usable, computer-usable, or computer-readable medium in any of a variety of forms, and that the present disclosure applies equally regardless of the particular type of instruction or signal bearing medium or storage medium utilized to actually carry out the distribution. Examples of machine usable/readable or computer usable/readable mediums include: nonvolatile, hard-coded type mediums such as read only memories (ROMs) or erasable, electrically programmable read only memories (EEPROMs), and user-recordable type mediums such as floppy disks, hard disk drives and compact disk read only memories (CD-ROMs) or digital versatile disks (DVDs).

Although an embodiment of the present disclosure has been described in detail, those skilled in the art will understand that various changes, substitutions, variations, and improvements disclosed herein may be made without departing from the spirit and scope of the disclosure in its broadest form.

None of the description in the present application should be read as implying that any particular element, step, or function is an essential element which must be included in the claim scope: the scope of patented subject matter is defined only by the allowed claims. Moreover, none of these claims are intended to invoke paragraph six of 35 USC § 112 unless the exact words "means for" are followed by a participle.

What is claimed is:

1. A method for secure acquisition and transmission of an image which comprises protected health information (PHI) by a mobile communication device, the method comprising:
   acquiring the PHI image by the mobile communication device;
   allocating volatile memory space in the mobile communication device for a session;
   digitally storing the acquired PHI image in the allocated volatile memory space;
   transmitting the digitally stored PHI image in the mobile communication device using a secure transmission protocol during the session;
   encrypting the digitally stored PHI image prior to transmission according to the secure transmission protocol; and
   de-allocating the volatile memory space at a termination of the session, wherein:
      the de-allocation of the volatile memory space causes the stored PHI image to not be persistently retained in the mobile communication device, and
      the non-persistent retention of the stored PHI image is in compliance with the Health Insurance Portability and Accountability Act (HIPAA).

2. The method of claim 1, wherein the volatile memory space is de-allocated by marking the volatile memory space as unallocated upon the termination.

3. The method of claim 1, wherein the digitally stored PHI image is transmitted to a remote server.

4. The method of claim 3, further comprising authenticating, employing the secure transmission protocol, the PHI image upon reception by the remote server.

5. The method of claim 1, further comprising acquiring the PHI image using a digital camera of the mobile communication device.

6. The method of claim 1, wherein the session is defined for a predetermined time period.

7. A system for secure acquisition and transmission of an image which comprises protected health information (PHI), the system comprising:
   a mobile communication device configured to communicate over a communication network, the mobile communication device comprising:
      at least one processor;
      a volatile memory space allocated by the at least one processor for a defined session and de-allocated at a termination of the defined session; and
      a digital camera configured to acquire the PHI image and to store the acquired PHI image in the allocated volatile memory space, wherein:
         during the defined session, the mobile communication device transmits the stored PHI image using a secure transmission protocol that encrypts the digitally stored PHI image prior to the transmission,
         the de-allocation of the volatile memory space causes the stored PHI image to not be persistently retained in the mobile communication device, and
         the non-persistent retention of the stored PHI image is in compliance with the Health Insurance Portability and Accountability Act (HIPAA).

8. The system of claim 7, wherein the encrypted PHI image is transmitted to a remote server and the secure transmission protocol authenticates the PHI image upon reception by the remote server.

9. The system of claim 7, wherein the volatile memory space is de-allocated by marking the volatile memory space as unallocated upon the termination.

10. The system of claim 7, wherein the volatile memory space is a random access memory (RAM).

11. The system of claim 7, wherein the defined session is defined for a predetermined time period.

12. A system for secure acquisition and transmission of an image which comprises protected health information (PHI), the system comprising:
   a mobile communication device configured to communicate over a communication network, the mobile communication device comprising:
      at least one processor;
      a volatile memory space allocated by the at least one processor for a defined session and de-allocated at a termination of the defined session; and
      a digital camera configured to acquire the PHI image and to store the acquired PHI image in the allocated volatile memory space; and
   a server, wherein:
      the mobile communication device transmits, during the defined session, the stored PHI image to the server over the communication network using a secure transmission protocol that encrypts the digitally stored PHI image prior to the transmission,
      the de-allocation of the volatile memory space causes the stored PHI image to not be persistently retained in the mobile communication device, and
      the non-persistent retention of the stored PHI image is in compliance with the Health Insurance Portability and Accountability Act (HIPAA).

13. The system of claim 12, wherein the de-allocation of the volatile memory space causes the stored PHI image to not be persistently retained in the mobile device.

14. The system of claim 12, wherein the volatile memory space is de-allocated by marking the volatile memory space as unallocated upon the termination.

15. The system of claim 12, wherein the defined session is defined for a predetermined time period.

* * * * *